(12) United States Patent
Kiani et al.

(10) Patent No.: US 12,235,947 B2
(45) Date of Patent: Feb. 25, 2025

(54) DISPLAY LAYOUT AND INTERACTIVE OBJECTS FOR PATIENT MONITORING

(71) Applicant: Masimo Corporation, Irvine, CA (US)

(72) Inventors: Massi Joe E. Kiani, Laguna Niguel, CA (US); Bilal Muhsin, Irvine, CA (US); Ammar Al-Ali, San Juan Capistrano, CA (US); Nicholas Evan Barker, Laguna Beach, CA (US); Chad A. DeJong, Los Angeles, CA (US); Omar Ahmed, Lake Forest, CA (US); Keith Ward Indorf, Lake Elsinore, CA (US); Steve Coon, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 18/474,071

(22) Filed: Sep. 25, 2023

(65) Prior Publication Data
US 2024/0095323 A1    Mar. 21, 2024

Related U.S. Application Data

(63) Continuation of application No. 17/072,963, filed on Oct. 16, 2020, now Pat. No. 11,803,623.
(Continued)

(51) Int. Cl.
*G06F 21/32* (2013.01)
*A61B 5/00* (2006.01)
(Continued)

(52) U.S. Cl.
CPC .............. *G06F 21/32* (2013.01); *G16H 10/60* (2018.01); *G16H 40/20* (2018.01); *G16H 40/67* (2018.01);
(Continued)

(58) Field of Classification Search
CPC ......... G06F 21/32; G06F 3/048; G16H 10/60; G16H 40/20; G16H 40/67; G16H 50/50; G16H 80/00; G16H 40/63; A61B 5/0024
See application file for complete search history.

(56) References Cited

U.S. PATENT DOCUMENTS 3,942,751 A  *  3/1976  Fay ................... F16M 11/2014
                                                248/598
4,960,128 A     10/1990  Gordon et al.
(Continued)

FOREIGN PATENT DOCUMENTS

AU   2016336420    6/2021
JP   2003-088561   3/2003
(Continued)

OTHER PUBLICATIONS

US 2022/0192529 A1, 06/2022, Al-Ali et al. (withdrawn)
(Continued)

*Primary Examiner* — Fekadeselassie Girma
*Assistant Examiner* — Mancil Littlejohn, Jr.
(74) *Attorney, Agent, or Firm* — Knobbe, Martens, Olson & Bear, LLP

(57) ABSTRACT

A physiological patient monitoring system with a patient-facing interface is disclosed. The patient interface can be used by the patient to communicate with hospital staff without actually requesting attendance and can request attendance for specific purposes. The patient interface may also track patient treatment and inform patients of the details of their treatments.

18 Claims, 21 Drawing Sheets

Related U.S. Application Data

(60) Provisional application No. 63/017,151, filed on Apr. 29, 2020, provisional application No. 62/923,248, filed on Oct. 18, 2019.

(51) Int. Cl.
  *G16H 10/60* (2018.01)
  *G16H 40/20* (2018.01)
  *G16H 40/67* (2018.01)
  *G16H 50/50* (2018.01)
  *G16H 80/00* (2018.01)

(52) U.S. Cl.
  CPC ............. *G16H 50/50* (2018.01); *G16H 80/00* (2018.01); *A61B 5/0024* (2013.01)

(56) References Cited

U.S. PATENT DOCUMENTS

| | | |
|---|---|---|
| 4,964,408 A | 10/1990 | Hink et al. |
| 5,319,355 A | 6/1994 | Russek |
| 5,319,747 A | 6/1994 | Gerrissen et al. |
| 5,337,744 A | 8/1994 | Branigan |
| 5,341,805 A | 8/1994 | Stavridi et al. |
| 5,377,676 A | 1/1995 | Vari et al. |
| 5,431,170 A | 7/1995 | Mathews |
| 5,436,499 A | 7/1995 | Namavar et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,590,649 A | 1/1997 | Caro et al. |
| 5,594,469 A | 1/1997 | Freeman et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| D385,547 S | 10/1997 | Snell |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| D394,852 S | 6/1998 | Levin |
| 5,758,644 A | 6/1998 | Diab et al. |
| 5,760,910 A | 6/1998 | Lepper, Jr. et al. |
| D395,878 S | 7/1998 | Copeland et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| D436,580 S | 1/2001 | Navano et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |

(56) References Cited

U.S. PATENT DOCUMENTS

| | | |
|---|---|---|
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| D656,946 S | 4/2012 | Judy |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| D693,835 S | 11/2013 | Daniel |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| D709,077 S | 7/2014 | Jonsson et al. |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,972,272 B1 | 3/2015 | Dvorak et al. |
| 8,989,831 B2 | 3/2015 | Al-Ali et al. |
| D726,205 S | 4/2015 | Angelides |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| D759,063 S | 6/2016 | Chen |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |

(56) References Cited

U.S. PATENT DOCUMENTS

| | | | |
|---|---|---|---|
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| D815,147 S | 4/2018 | Linzie et al. |
| D815,661 S | 4/2018 | Anzures et al. |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| D826,258 S | 8/2018 | Silva |
| D830,412 S | 10/2018 | Linzie et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,579,245 B1 | 3/2020 | White |
| 10,608,817 B2 | 3/2020 | Haider et al. |
| D880,477 S | 4/2020 | Forrest et al. |
| D881,225 S | 4/2020 | Elgena et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D895,678 S | 9/2020 | Levy |
| D895,679 S | 9/2020 | Levy |
| D896,271 S | 9/2020 | Levy |
| D896,839 S | 9/2020 | Levy |
| D896,840 S | 9/2020 | Levy |
| D897,098 S | 9/2020 | Al-Ali |
| D897,372 S | 9/2020 | Levy |
| 10,779,098 B2 | 9/2020 | Iswanto et al. |
| D899,449 S | 10/2020 | Essex |
| D900,872 S | 11/2020 | Fixler et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D924,264 S | 7/2021 | Chou et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| D937,875 S | 12/2021 | Harvey |
| D938,961 S | 12/2021 | Hui |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |

(56) References Cited

U.S. PATENT DOCUMENTS

| | | |
|---|---|---|
| D950,583 S | 5/2022 | Zimmer et al. |
| D950,599 S | 5/2022 | Ahmed |
| D950,738 S | 5/2022 | Al-Ali et al. |
| 11,354,018 B2 | 6/2022 | Canneto et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D974,411 S | 1/2023 | Fogu |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| D986,260 S | 5/2023 | Hui |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| D999,776 S | 9/2023 | Dahl et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,010,680 S | 1/2024 | Dahl et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,030,789 S | 6/2024 | Kuwatani |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,133,717 B2 | 11/2024 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0172789 A1 | 7/2008 | Elliot et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0037170 A1* | 2/2010 | Poole .................. G06F 3/0481 715/772 |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0089419 A1 | 4/2012 | Huster |
| 2012/0092162 A1 | 4/2012 | Rosenberg |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0253951 A1* | 9/2013 | Richter .................. G16H 10/60 705/2 |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0188516 A1 | 7/2014 | Kamen et al. |
| 2014/0257852 A1* | 9/2014 | Walker .................. G06Q 10/10 705/3 |
| 2014/0275871 A1 | 9/2014 | Lamego et al. |

(56) References Cited

U.S. PATENT DOCUMENTS

| | | |
|---|---|---|
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0294549 A1 | 10/2015 | Ribble |
| 2016/0180694 A1 | 6/2016 | Rosenberg |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0258669 A1 | 9/2018 | Moock et al. |
| 2018/0310823 A1 | 11/2018 | Al-Ali et al. |
| 2019/0117070 A1 | 4/2019 | Muhsin et al. |
| 2019/0178010 A1 | 6/2019 | Moock et al. |
| 2019/0189258 A1 | 6/2019 | Barrett |
| 2019/0239787 A1 | 8/2019 | Pauley et al. |
| 2019/0320906 A1 | 10/2019 | Olsen |
| 2019/0374713 A1 | 12/2019 | Kiani et al. |
| 2019/0385753 A1* | 12/2019 | Aganyan ............... G16H 15/00 |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0204631 A1 | 6/2020 | Subramaniam et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2021/0407658 A1 | 12/2021 | Taheri et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0359088 A1 | 11/2022 | Vasalos |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0252046 A1 | 8/2024 | Jansen et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |

FOREIGN PATENT DOCUMENTS

| | | |
|---|---|---|
| JP | 2006-019841 | 1/2006 |
| JP | 2007-260072 | 11/2007 |
| JP | 2014-171776 | 9/2014 |
| JP | 2016-184427 | 10/2016 |
| JP | 2017-146936 | 8/2017 |
| JP | 2018-018531 | 2/2018 |
| JP | 2019-075148 | 5/2019 |
| WO | WO 2011/001248 | 1/2011 |
| WO | WO 2014/059521 | 4/2014 |
| WO | WO 2021/077019 | 4/2021 |
| WO | WO 2023/229980 | 11/2023 |

OTHER PUBLICATIONS

US 2024/0016391 A1, 01/2024, Lapotko et al. (withdrawn)
International Search Report and Written Opinion received in PCT Application No. PCT/US2020/056158. dated Jan. 28, 2021 in 15 pages.

(56) References Cited

OTHER PUBLICATIONS

How to Write Lab Value Skeleton Diagrams, Apr. 7, 2017, YouTube.com, retrieved Jul. 16, 2024, https://www.youtube.com/watch?v=I2f2UdiMXao, pp. 1.

Hunt, Justin, Lab Fishbone Creator, Sep. 27, 2019, YouTube.com, retrieved Jul. 16, 2024, https://www.youtube.com/watch?v=8AX_JDCpZeM, pp. 1.

Lab Fishbone Creator APK, Aug. 15, 2020, ChipApk.com, retrieved Jul. 16, 2024, https://chipapk.com/app/7814806/, pp. 4.

Resley, Justin, Live Vue by Spectrum Medical, May 30, 2023, Linked In.com, retrieved Jul. 16, 2024, https://www.linkedin.com/posts/justin-resley-ccp-emeritus-85a16869_patientsafety-medical-leader-activity-7069351136243191808-NkXj/, pp. 1.

\* cited by examiner

DISPLAY LAYOUT AND INTERACTIVE OBJECTS FOR PATIENT MONITORING

CROSS REFERENCE TO PRIORITY APPLICATIONS

Any and all applications for which a foreign or domestic priority claim is identified in the Application Data Sheet as filed with the present application are hereby incorporated by reference under 37 CFR § 1.57. This application is a continuation of U.S. patent application Ser. No. 17/072,963, filed Oct. 16, 2020, entitled "DISPLAY LAYOUT AND INTERACTIVE OBJECTS FOR PATIENT MONITORING," now U.S. Pat. No. 11,803,623, which claims the benefit of priority to U.S. Provisional Patent Application No. 62/923,248, filed Oct. 18, 2019, entitled "DISPLAY LAYOUT AND INTERACTIVE OBJECTS FOR PATIENT MONITORING," and to U.S. Provisional Patent Application No. 63/017,151, filed Apr. 29, 2020, entitled "DISPLAY LAYOUT AND INTERACTIVE OBJECTS FOR PATIENT MONITORING." All the foregoing are hereby incorporated by reference in their entireties herein.

BACKGROUND

The present disclosure relates to display layouts and interactive objects for a physiological patient monitoring system.

Often patients have lackluster experiences at hospitals, regardless of the quality of treatment or the reputation of the hospital. Patients often do not feel informed enough about their treatments or do not feel they are receiving the right amount of attention. This leads to patients feeling confused or detached from their treatment. The problem is caused at least in part by the fact that the current hospital system has many inefficiencies that use care team members' time ineffectively. For example, most hospitals currently only have a general attendance button used for both non-emergencies, such as a request for a glass of water, as well as life-threatening events. Medical staff are thus wasting their time running between rooms for attendance requests that should be directed toward support staff. Further, entire teams of healthcare professionals take care of a single patient, but in the current hospital system, information is not shared in a way that allows every member to stay up to date on the patient's treatment and progress. Such gaps in knowledge mean not only that patients are not receiving answers when they ask questions, but there is a heightened risk of clinician error each time a new care team member arrives. Thus, there is a need for more effective and efficient channels of communication between hospital staff and patients.

SUMMARY

For purposes of summarizing the disclosure, certain aspects, advantages and novel features are discussed herein. It is to be understood that not necessarily all such aspects, advantages, or features will be embodied in any particular configuration of the invention and an artisan would recognize from the disclosure herein a myriad of combinations of such aspects, advantages or features.

The disclosure describes a physiological patient monitoring system with a patient-facing interface. The patient interface can be used by the patient to communicate with hospital staff without actually requesting attendance and can request attendance for specific purposes such that physicians and nurses are not running room to room for non-medical emergency needs. The patient interface can also track patient treatment and informs patients of the details of their treatments, thereby increasing engagement.

BRIEF DESCRIPTION OF THE DRAWINGS

Throughout the drawings, reference numbers may be re-used to indicate correspondence between referenced elements. The drawings are provided to illustrate example configurations described herein and are not intended to limit the scope of the disclosure.

DETAILED DESCRIPTION OF THE PREFERRED CONFIGURATION

The current hospital system has several inefficiencies, many of which are caused by ineffective communication. Such ineffective communication leads to negative patient experience because patients feel confused and detached from their treatment. Patients are ill-informed about the details of their treatment, and they cannot communicate their needs until a hospital staff member, who may not be the best person for the patient's particular need, is already in the room. The presently disclosed patient interface of a physiological patient monitoring system addresses the issue of inefficient communication by creating a portal through which patients can both track details about their treatment and communicate their exact needs to the most relevant members of the hospital staff. By fostering quick yet precise communication, the present system aims to improve patient hospital experiences and increase patient understanding and engagement in treatments. Furthermore, physical switches may be heard to reach or the wires may be cumbersome. Accordingly, the systems described herein can improve communication without requiring physical switches that a patient may need to try to access to get help. In some instances, there are no physical switches and/or wires to call a nurse or indicate status in the hospital room.

Figure 1:
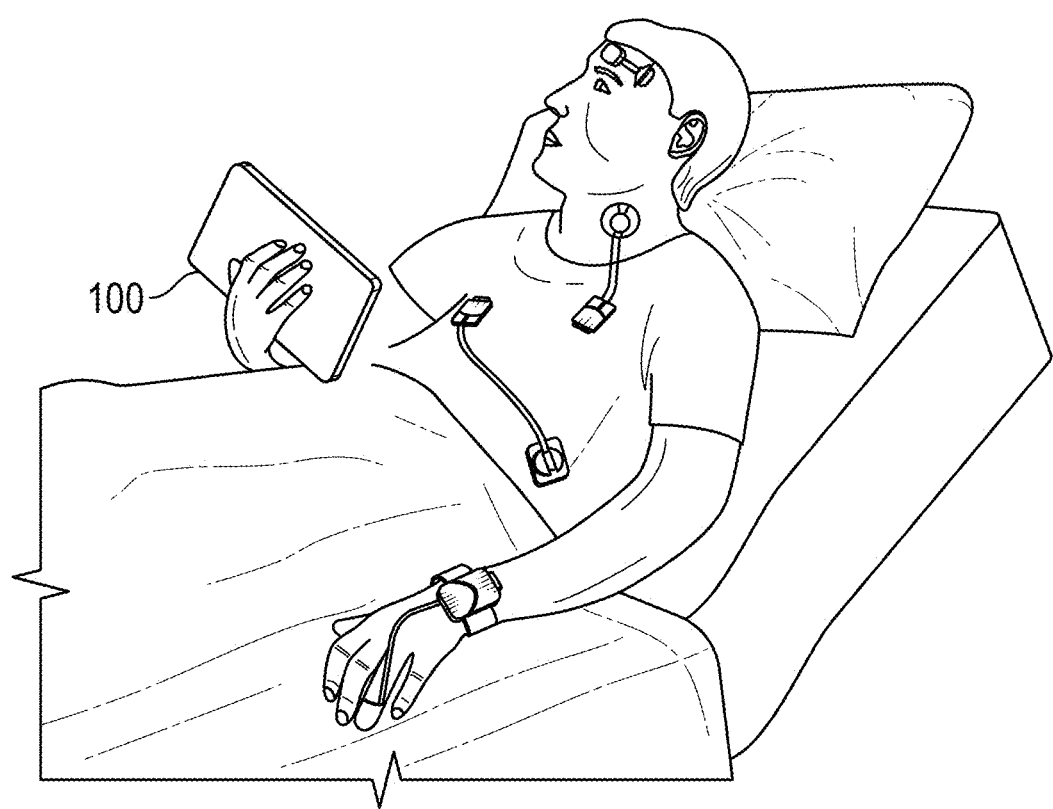
FIG. 1 depicts a hospital patient using a portable device with a patient interface for a physiological monitoring system.

FIG. 1 depicts a hospital patient using a portable device 100 with a patient interface for a physiological patient monitoring system. The physiological patient monitoring system may be connected to patient monitoring equipment and a hospital data network such that the patient interface may be updated with live measurements, diagnoses, and treatment plans. Updates may occur continuously, automatically, and/or only when new data is manually entered. Patients may thus be more informed about and involved with their treatment and progress. Patients may also communicate with hospital staff and request attendance from their hospital beds through the physiological patient monitoring system. The system may route patient requests to the appropriate hospital department based on the content of the patient's request.

Figure 2:
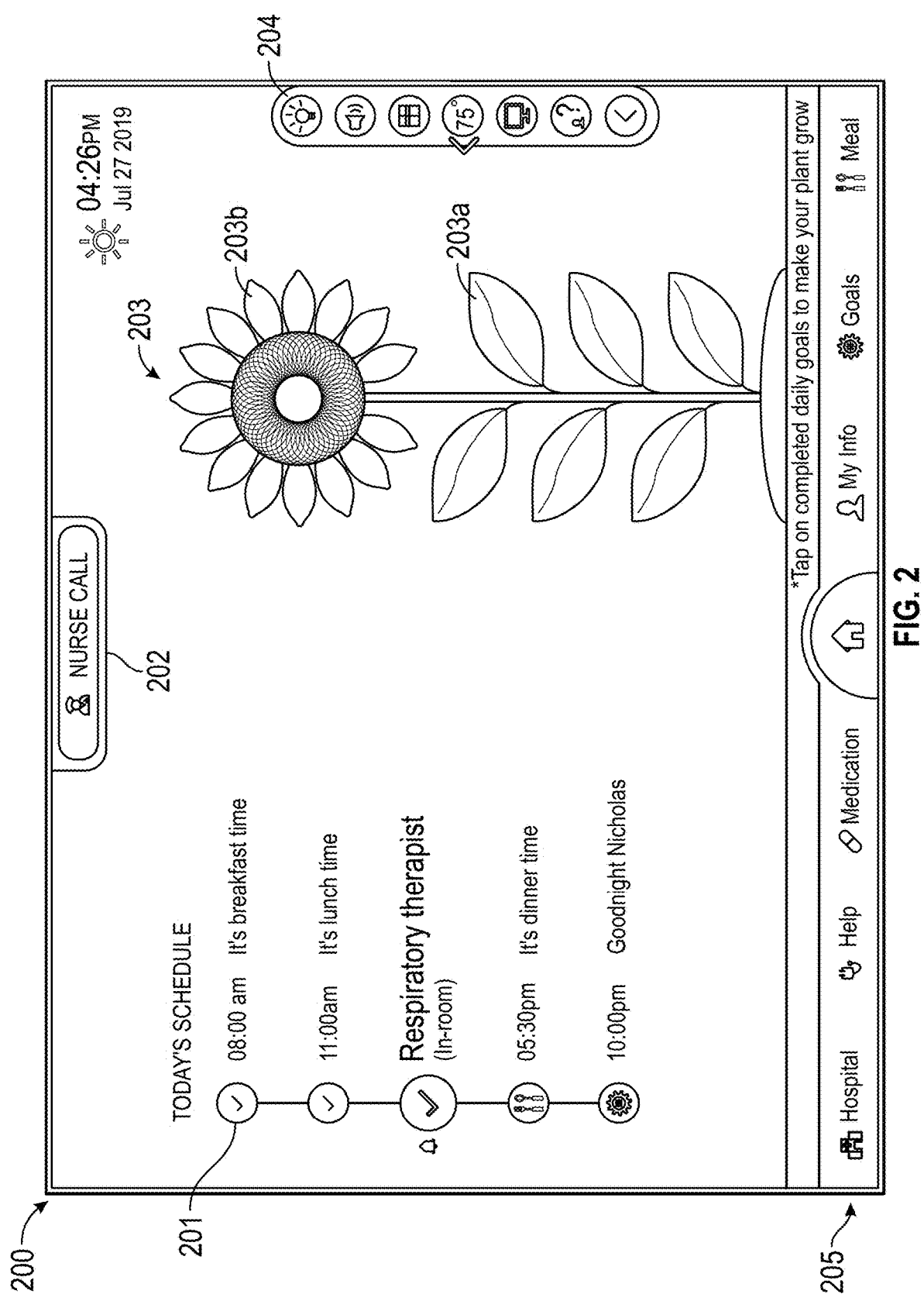
FIG. 2 is an illustrative interface for a default screen for a patient interface on portable devices in hospital rooms, according to some configurations.

FIG. 2 illustrates an example default screen 200 for a patient interface for portable devices in hospital rooms. The default screen 200 may display a patient's daily schedule 201, nurse call button 202, progress measurement feature 203, room control panel 204, and application navigation panel 205. The application navigation panel 205 may be used to access all other pages of the application. To return to the default screen 200, the patient may simply tap on the home button in the navigation panel 205. For ease of access, the nurse call button 202 may remain in the same location on each screen of the application. The daily schedule 201 may show the time at which each task is set to occur. The daily schedule 201 may update automatically once the scheduled time for an event has passed, or it may only mark a task as complete when the patient, a healthcare provider, or both manually mark the task as complete. In some configurations, the progress measurement feature 203 may be shaped like a flower that grows as daily tasks are completed. A leaf 203a may be added for completed tasks and the flower 203b may bloom when all tasks are complete. Other configurations may assign different parts of the flower to completed tasks, contain more or less detailed parts of the flower, or may use a different graphical representation of patient progress altogether. Together, the daily schedule 201 and the progress measurement feature 203 can inform and motivate patients throughout their recovery. The room control panel 204 may be partially hidden when not in use.

Figure 3:
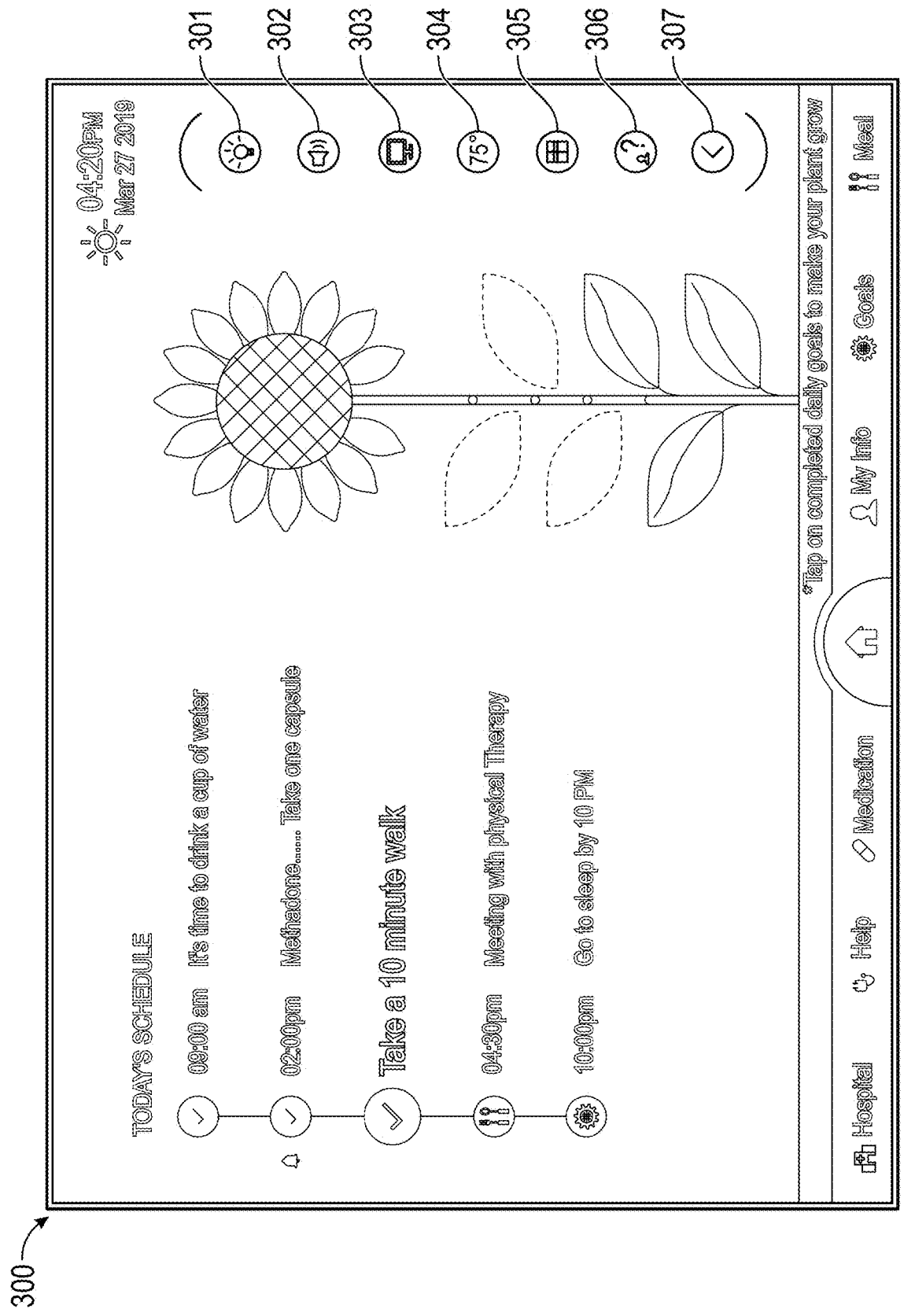
FIG. 3 is an illustrative interface for a room control panel summon screen where the room control panel appears in full view while the remaining screen features are dimmed, according to some configurations.

FIG. 3 shows an example room control panel summon screen 300 where the room control panel 204 shown in FIG. 2 may appear in full view while the remaining screen features are dimmed. The room control panel can allow patients to control the light 301, television or speaker volume 302, television 303, temperature 304, and window blinds 305 without calling hospital staff or even leaving their beds. The control panel may also include a help button 306 which explains how to use the application. The call-out button 307 can open the control panel as its own full screen.

Figure 4:
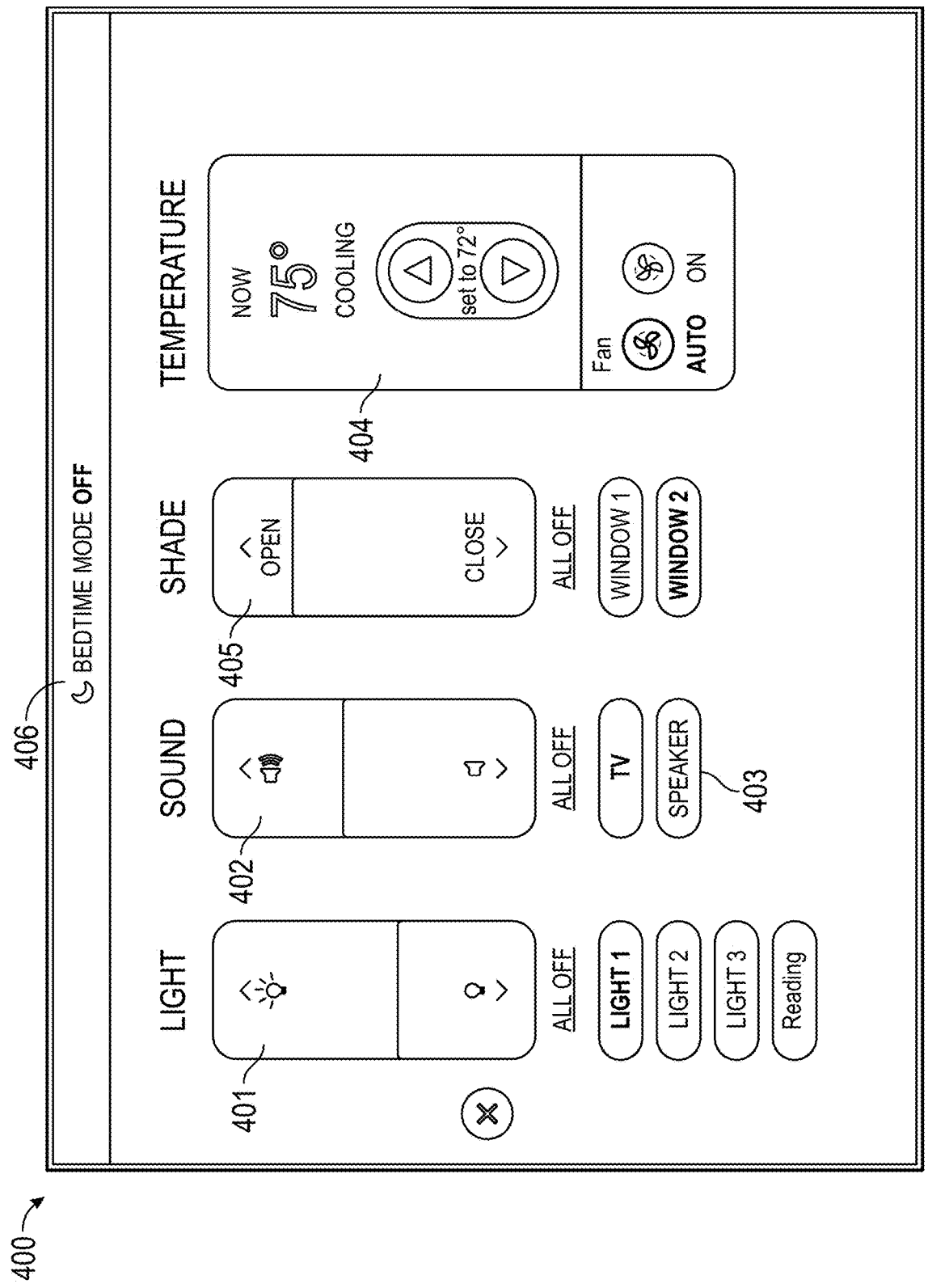
FIG. 4 is an illustrative interface for a full screen view of a room control panel according to some configurations.

FIG. 4 shows an illustrative full screen view 400 of the room control panel 204 from FIG. 2. The same features that were in the sidebar view may appear on this screen in full: light 401, volume 402, television 403, temperature 404, and window blinds 405. The full screen view 400 may include detailed buttons that allow more specific control of the features, such as which individual light to adjust, which window's blind to move, or other such changes to individual ambient items. The full screen view 400 of the room control panel can have an extra bedtime mode button 406. Bedtime mode may darken the screen such that patients can sleep without blue light disruption. With greater control over their hospital room environment, patients may not need to call for hospital staff assistance as often, thereby freeing up healthcare providers to attend to more urgent matters. Patients may also feel more comfortable as they can make adjustments to their liking at any time.

Figure 5:
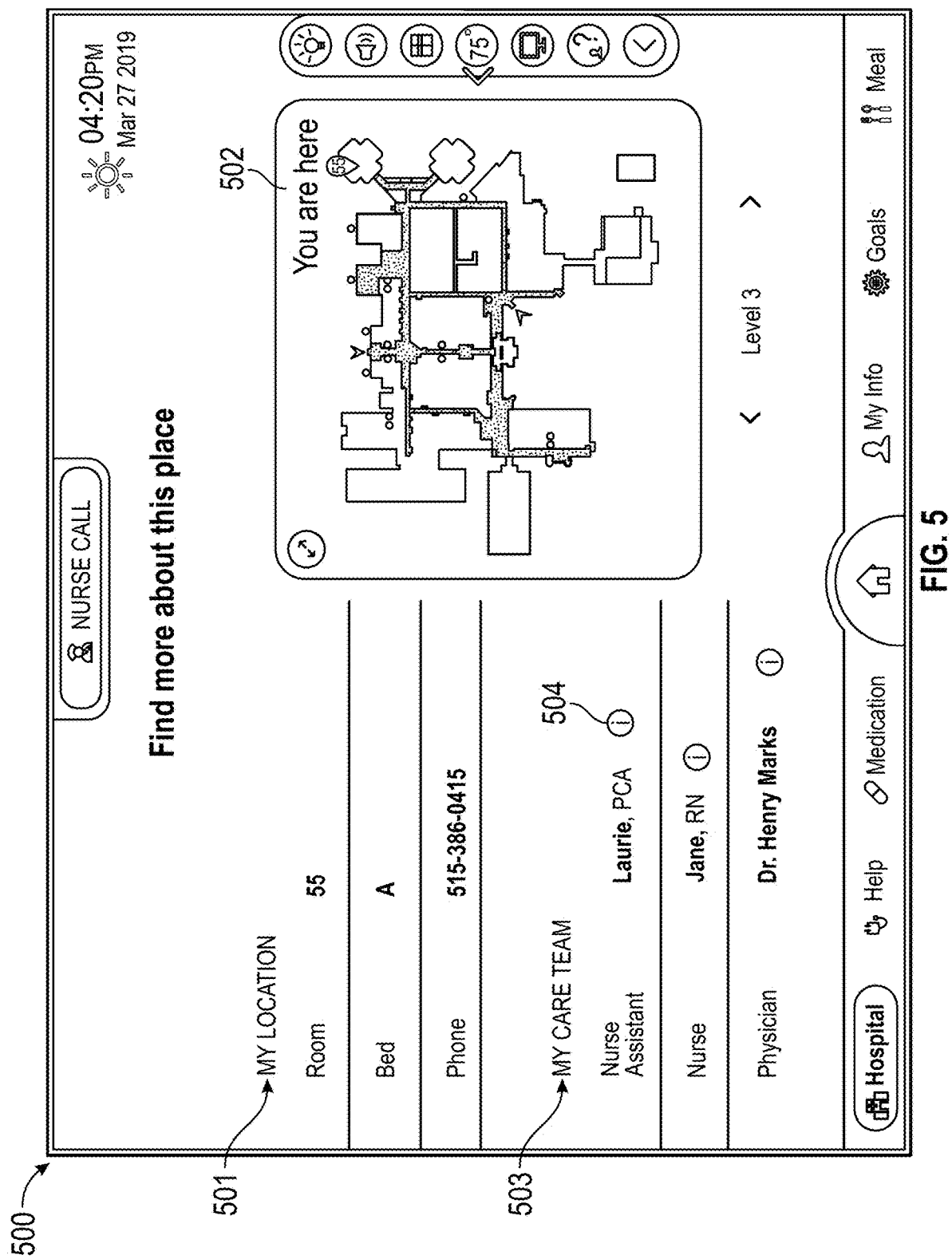
FIG. 5 is an illustrative interface displaying personalized information regarding a hospital building and a patient's care staff, according to some configurations.

FIG. 5 illustrates an illustrative Hospital tab screen 500 which may display personalized information regarding the hospital building and the patient's care staff. The Hospital screen 500 may be accessed via the application navigation panel 205. The Hospital tab may show the patient's room information 501 and a hospital map 502. The patient's care team information 503 may also be included. The information button 504, when pressed, may create a pop-up or separate sub-screen that shares the individual team member's credentials, background, and any other information the team member chooses to share so that patients feel more connection with their care team.

Figure 6:
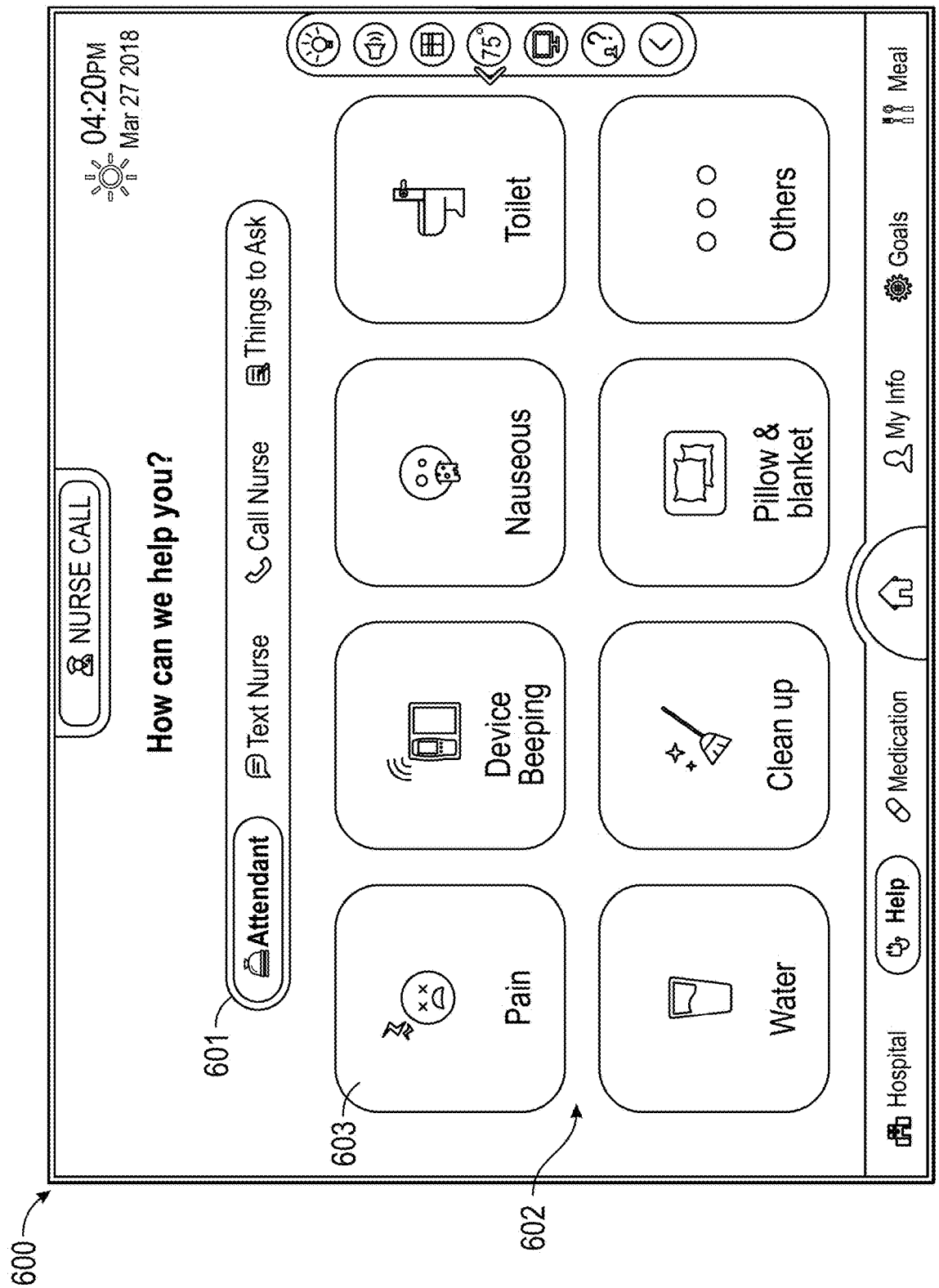
FIG. 6 is an illustrative interface of different methods patients may utilize to communicate with hospital staff, according to some configurations.

FIG. 6 shows a default Help tab screen 600, according to some configurations. The Help screen 600 may be accessed via the application navigation panel 205. The top control panel 601 may lead to sub-screens that allow patients to request staff assistance, contact a nurse, or write down questions to ask a care team member. The assistance buttons 602 may allow patients to specify the reason they need assistance, such that the appropriate hospital staff can be sent to the patient's room. In some configurations, when the patient selects an assistance button 602, a pop-up window or sub-screen may appear in which the patient can enter details about the selection. For example, after selecting the "nauseous" button, the physiological patient monitoring system may prompt the patient about the type of nausea, other discomfort associated with the nausea, etc. The physiological patient monitoring system may present pre-set options from which the patient may select, or the patient may freely type in details. Upon receiving user input, the physiological patient monitoring system may send an alert to one or more pagers, computing devices, portable electronic devices, or any other type of electronic device. The one or more electronic devices may be associated with a department in the hospital or with specific hospital staff. In some configurations, an individual electronic device may have a static pairing with one or more of the assistance buttons 602. In other configurations, the button-device pairings may be configurable, such that the individual electronic device may be used in different departments or by different hospital staff members. With the current predominant system, patients have one universal button that pages the nursing staff, even though most patient pages are non-emergencies, such as bedding adjustments, room operation questions, food requests, or cleaning requests. The assistance buttons 602 can save nurses and physicians time by sending the appropriate hospital staff from the start.

Figure 7A:
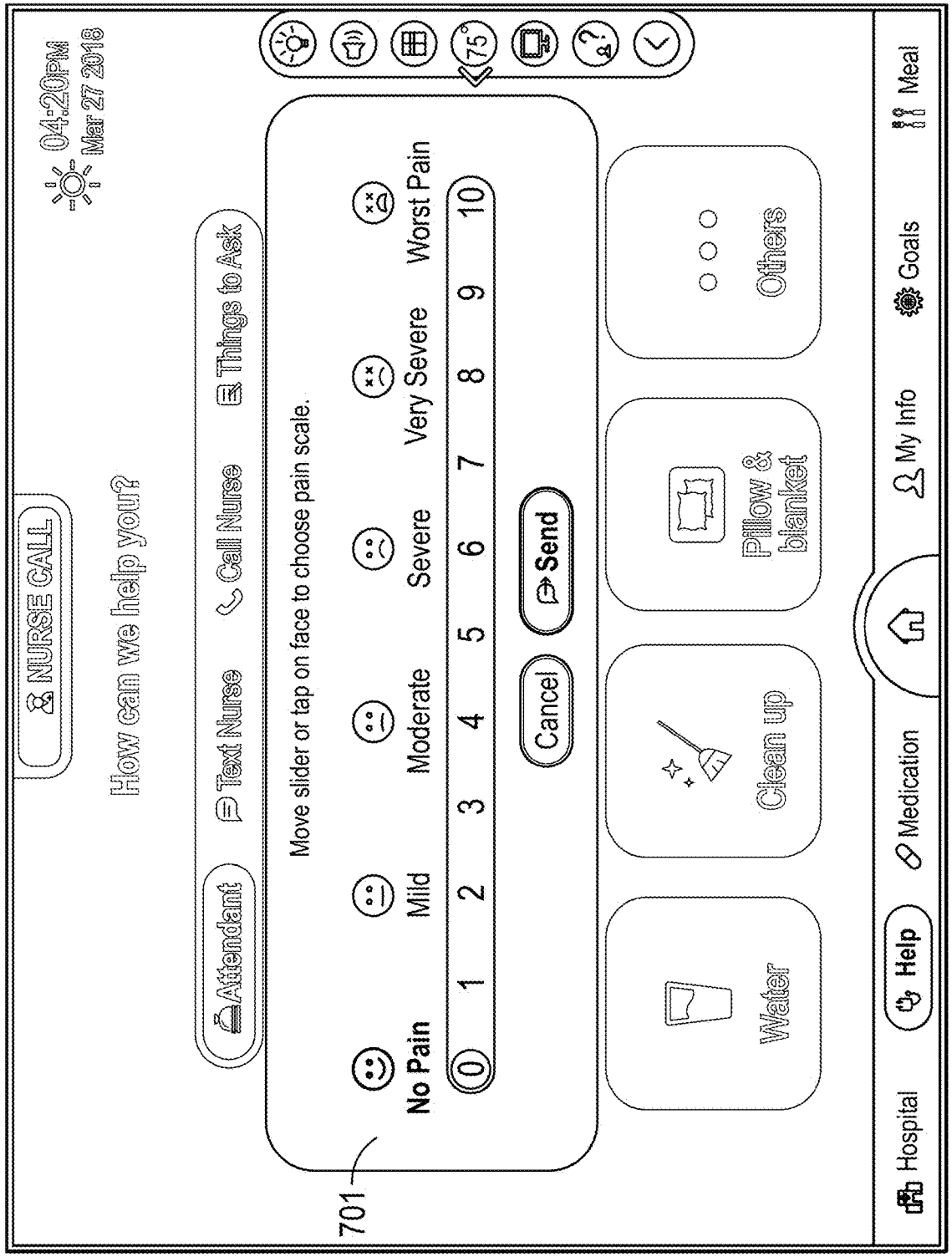
FIGS. 7A-7C are illustrative interfaces showing how patients could communicate their levels of pain while requesting attendance, according to some configurations.
Figure 7B:
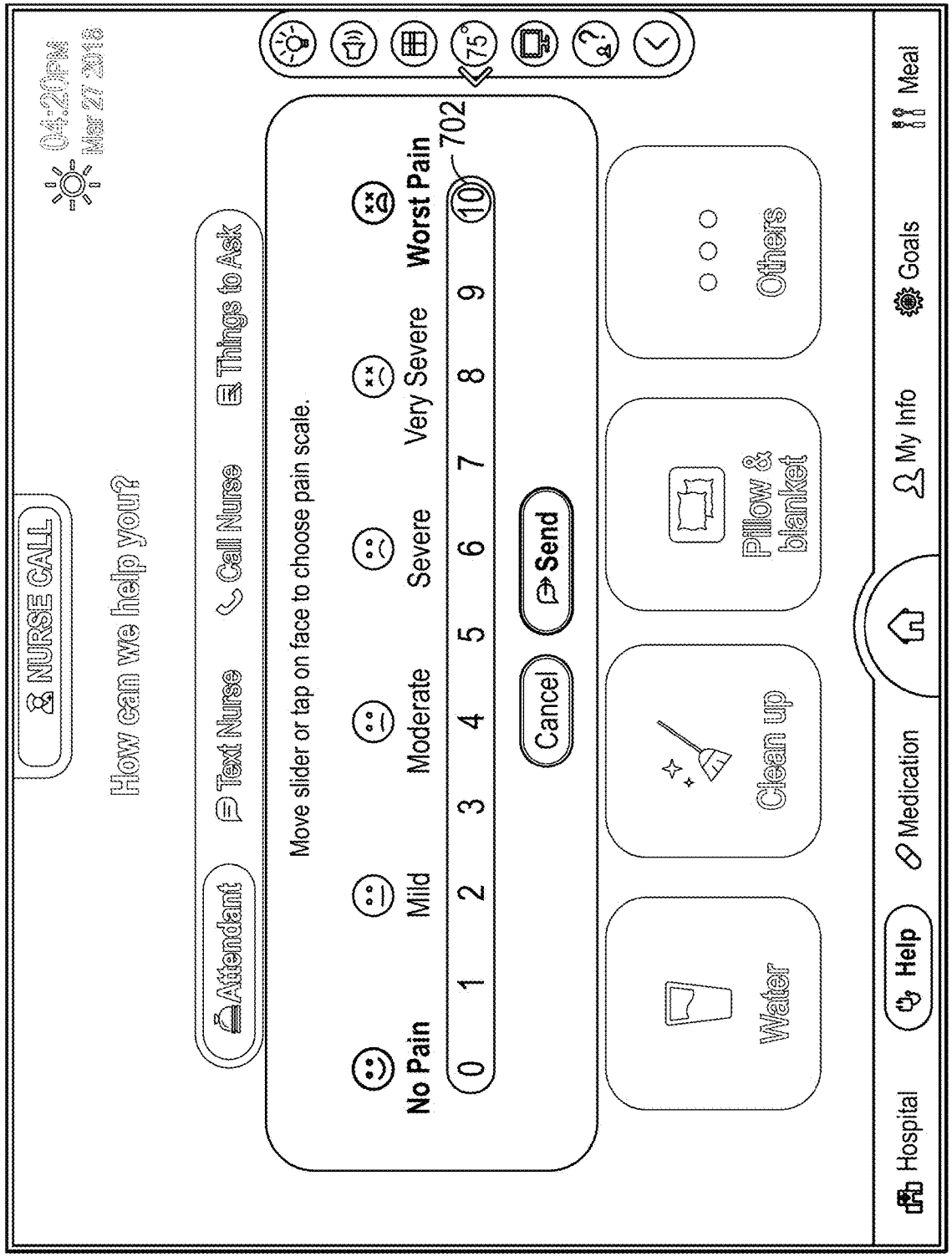
Figure 7C:
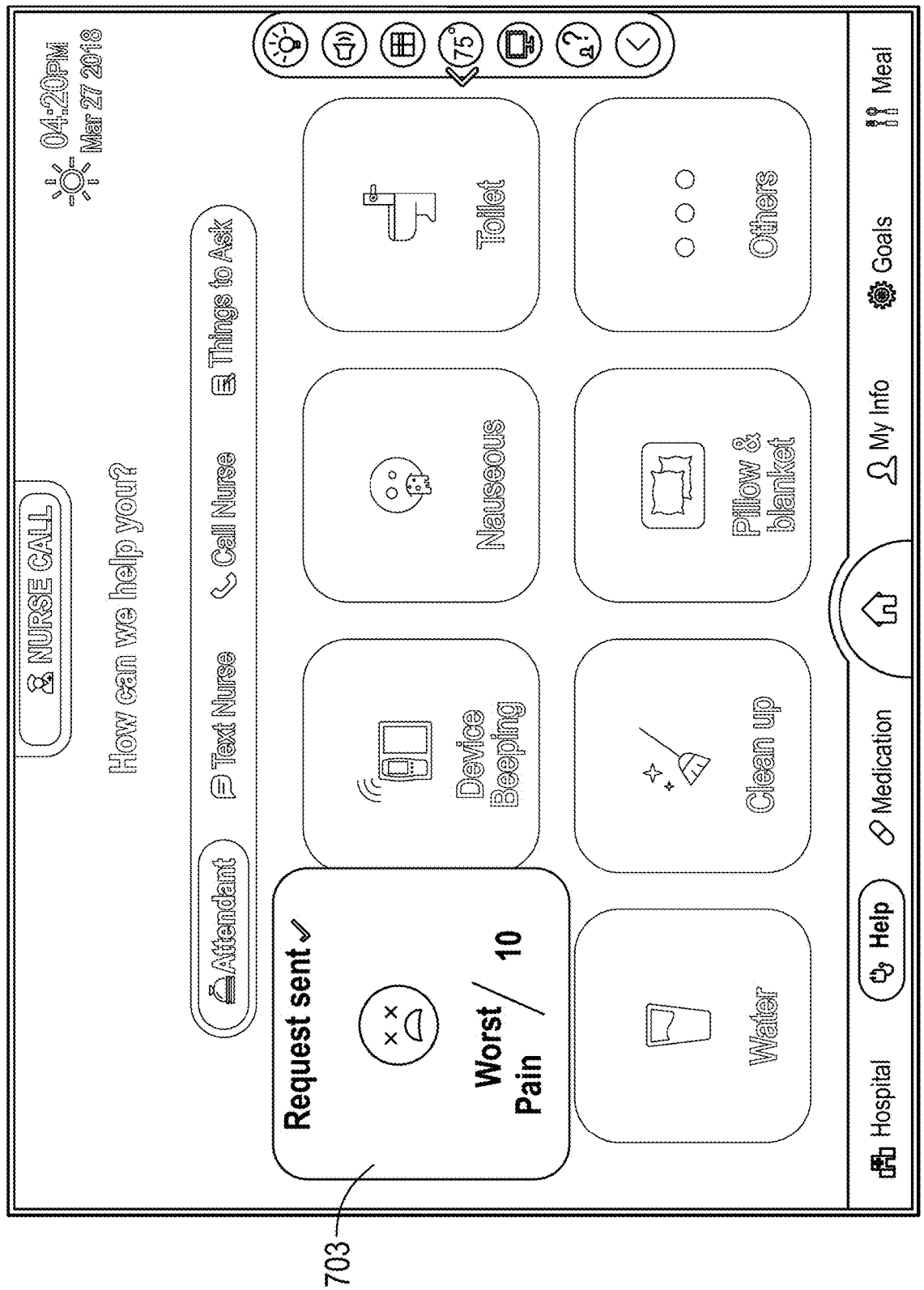

FIGS. 7A-7C illustrate how the Pain button 603 in FIG. 6 may work. FIG. 7A shows the pop-up 701 that may appear when the patient requests attendance due to pain. The pop-up 701 may be a numerical scale that reflects the severity of a patient's experienced pain. The numerical scale may span any number range and may be marked with any regular increment. In some configurations, the numerical scale may be controlled by a slider on a sliding scale rather than discrete buttons on an incremented scale. In some configurations, the pop-up may only display figures that reflect degrees of discomfort, may only contain descriptor words that reflect degrees of discomfort, or may be any other scale that allows patients to communicate their discomfort level. FIG. 7B illustrates how the graphics may update to reflect a patient selection 702. In some configurations, the pop-up may offer further patient prompts, such as location of pain, type of pain, duration of pain, etc. The physiological patient monitoring system may present pre-set options from which the patient may select, or the patient may freely type in details. In some configurations, the pop-up 701 may be a separate sub-screen. FIG. 7C shows an example of an updated Pain button 703 after the patient selection 702 is sent. The updated Pain button 703 may show the patient's selection and confirm the information was submitted.

Figure 8A:
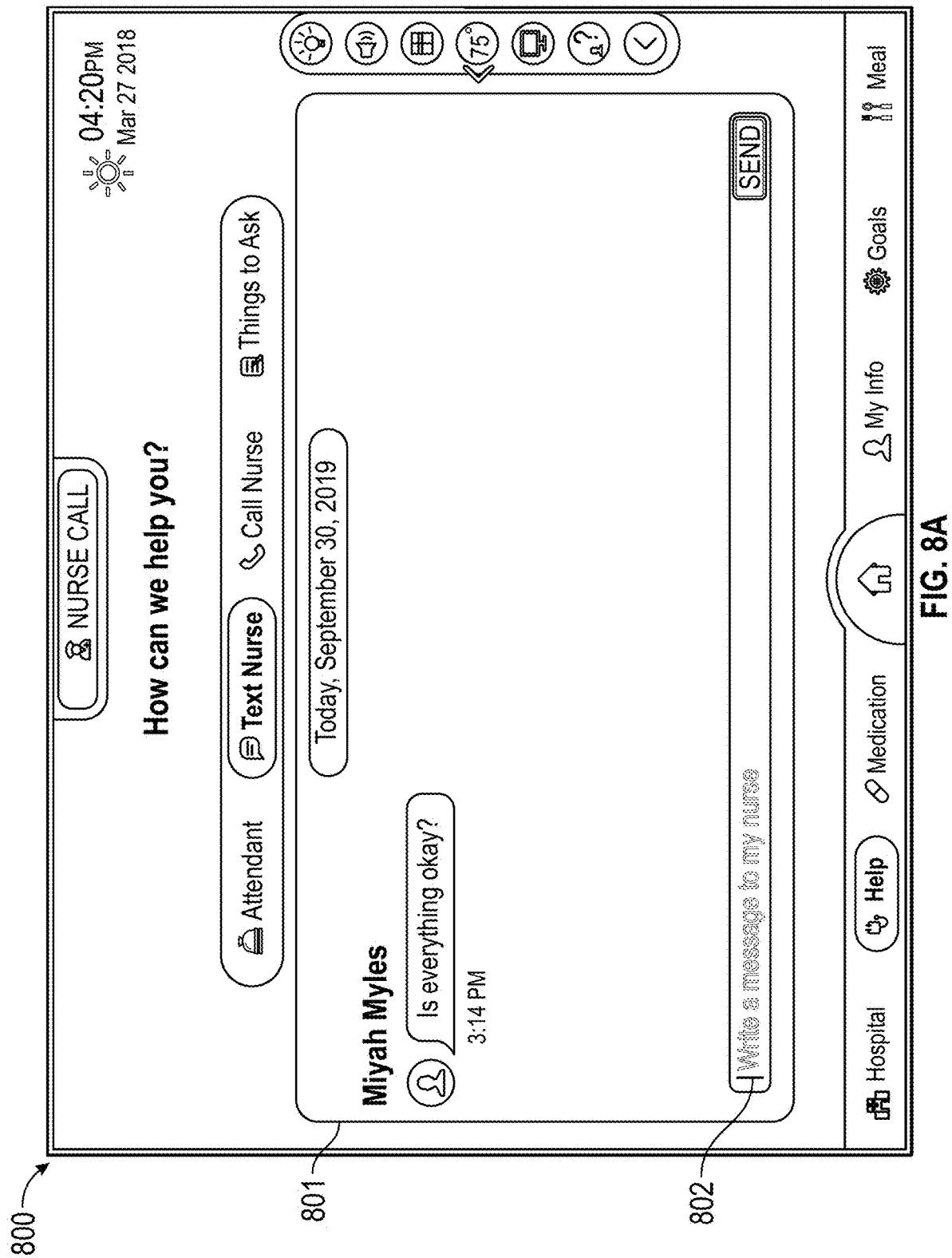
FIGS. 8A-8B are illustrative interfaces for a feature which allows patients to communicate with their assigned nurse via text messaging, according to some configurations.
Figure 8B:
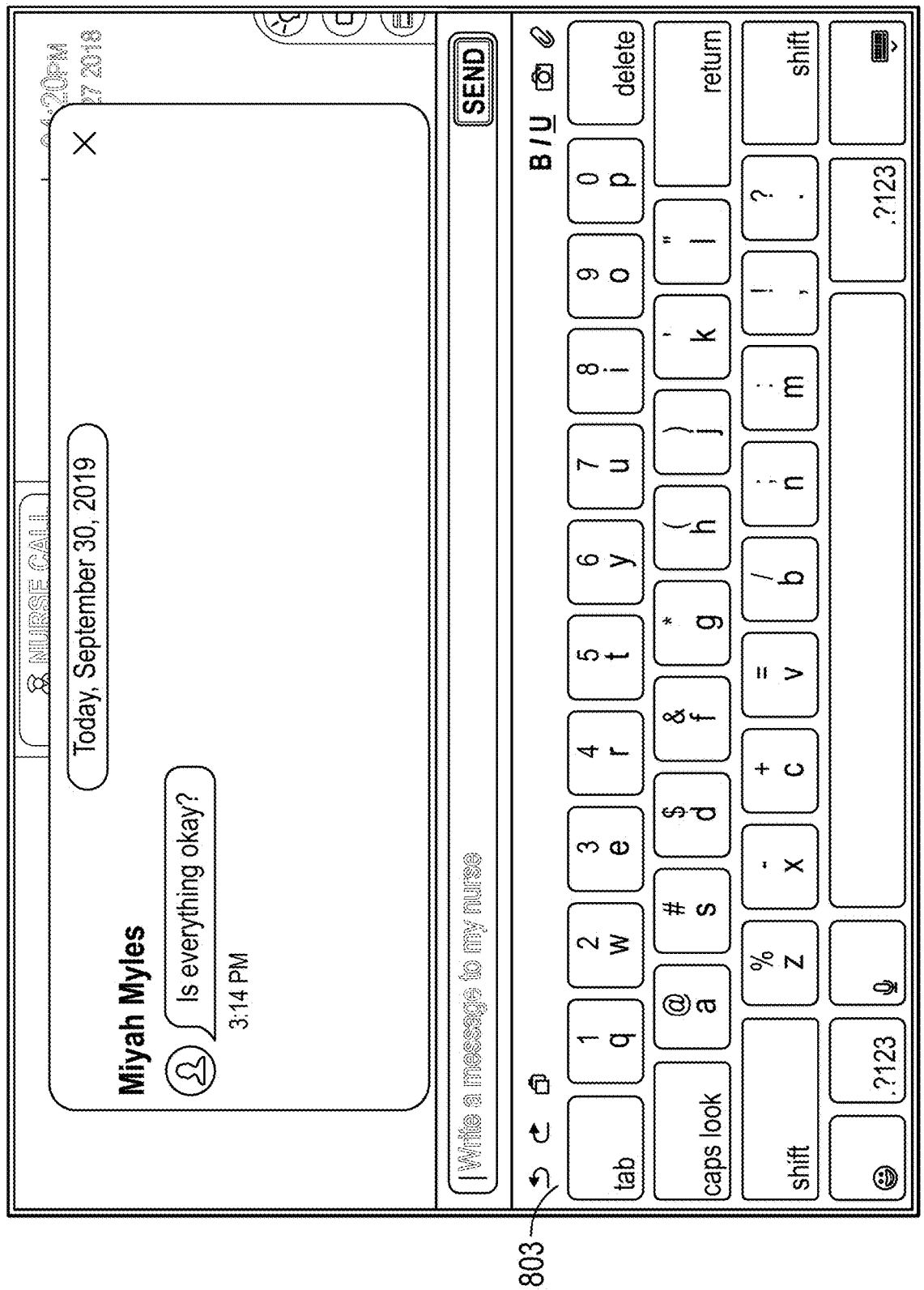

FIGS. 8A-8B illustrate an example Text Nurse sub-screen 800, which may be accessed through the control panel 601. FIG. 8A shows an illustrative chat window 801 which may open when the patient chooses Text Nurse. The chat function may be linked to an application on the nurse's cellular phone or other electronic device so that the nurse can receive live notifications and can provide live feedback. The Text Nurse feature may be linked to a device only accessible by the patient's attending nurse or may be linked to a general nursing department device such that any nurse may respond to the patient. FIG. 8B demonstrates an example virtual keyboard 803 that may appear when the patient taps on a message drafting space 802 on the chat window 801.

Figure 9:
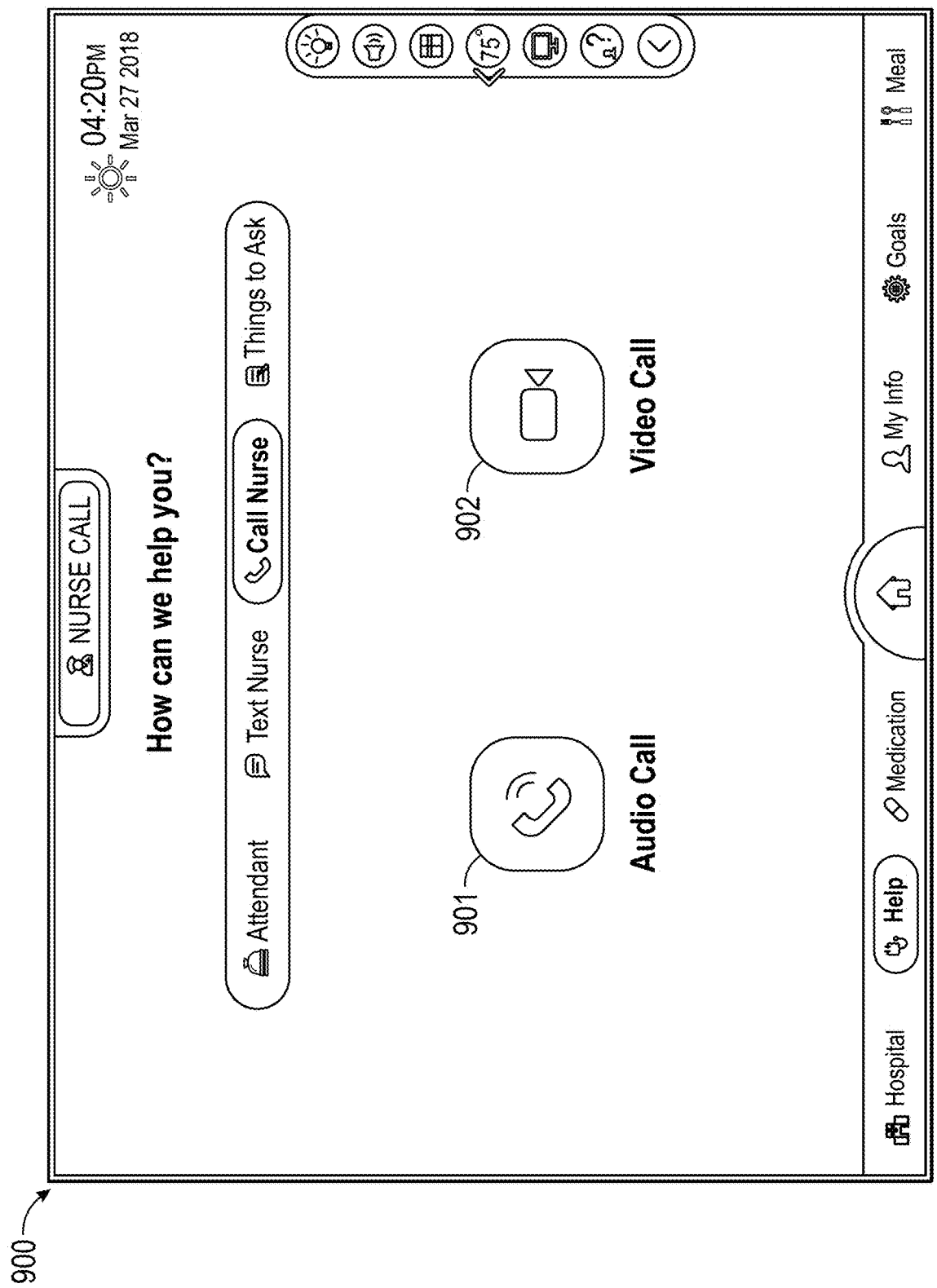
FIG. 9 is an illustrative interface for a feature which allows patients to communicate with their assigned nurse via either audio or video communication, according to some configurations.

FIG. 9 illustrates an example Call Nurse sub-screen 900, which may be accessed through the control panel 601. The sub-screen may offer the options to either audio call 901 or video call 902 the nurse. The portable device 100 may thus have a microphone, a camera, or both such that the patient can call the nurse. If the portable device 100 does not support audio or video transmission, the call buttons may be disactivated or a warning pop-up may appear when the buttons are selected. Both call options may be linked to an application on the nurse's cellular phone or other electronic device so that the nurse can receive live notifications and can provide live feedback. The Call Nurse feature may be linked to a device only accessible by the patient's attending nurse or may be linked to a general nursing department device such that any nurse may respond to the patient.

Figure 10:
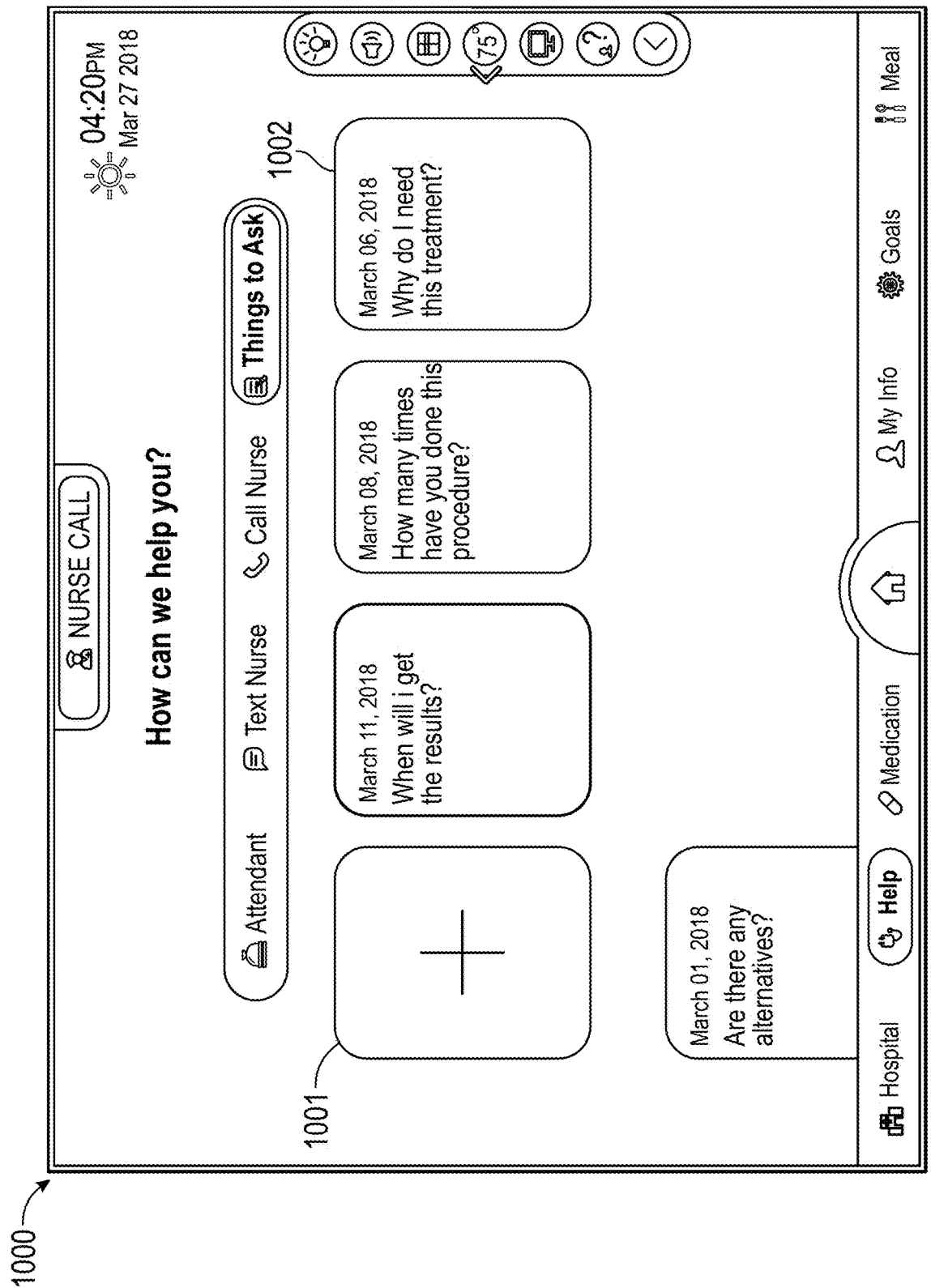
FIG. 10 is an illustrative interface for a feature which allows patients to record questions to ask hospital staff, according to some configurations.

FIG. 10 illustrates an example Things To Ask sub-screen 1000, which may be accessed through the control panel 601. The Things To Ask sub-screen 1000 can function like a digital notepad where the patient can create new questions 1001 and view saved questions 1002. In some configurations, patients may be able to select a specific individual on their care team to direct each question. Saving questions until the staff's scheduled visit may be more efficient than paging staff members each time the patient thinks of a question. In some configurations, the patient interface of the physiological patient monitoring system may be linked to a healthcare provider interface such that healthcare providers may directly access the patient's questions from a separate electronic device.

Figure 11A:
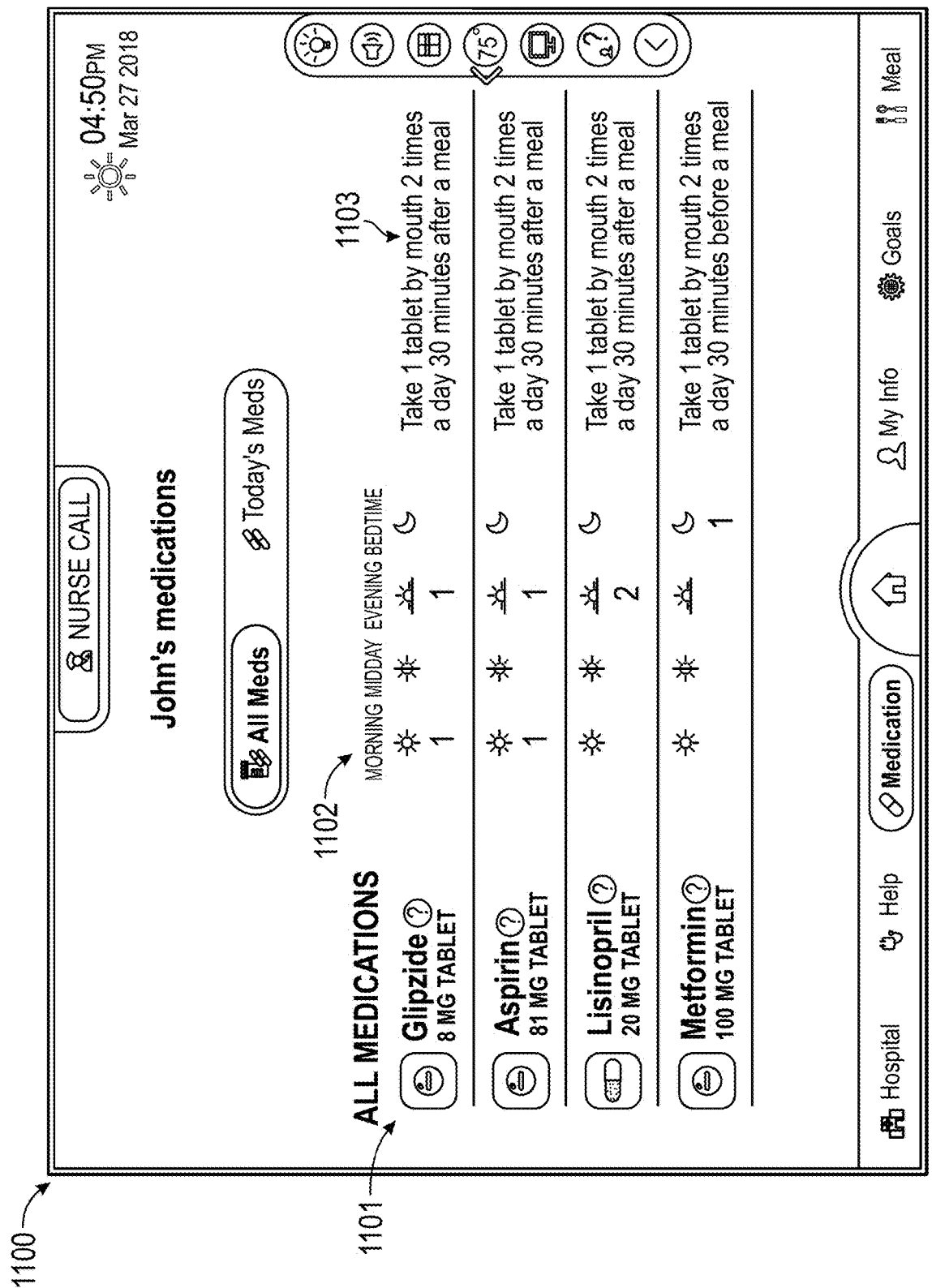
FIGS. 11A-11B are illustrative interfaces showing medication prescription and administration details for a patient, according to some configurations.
Figure 11B:
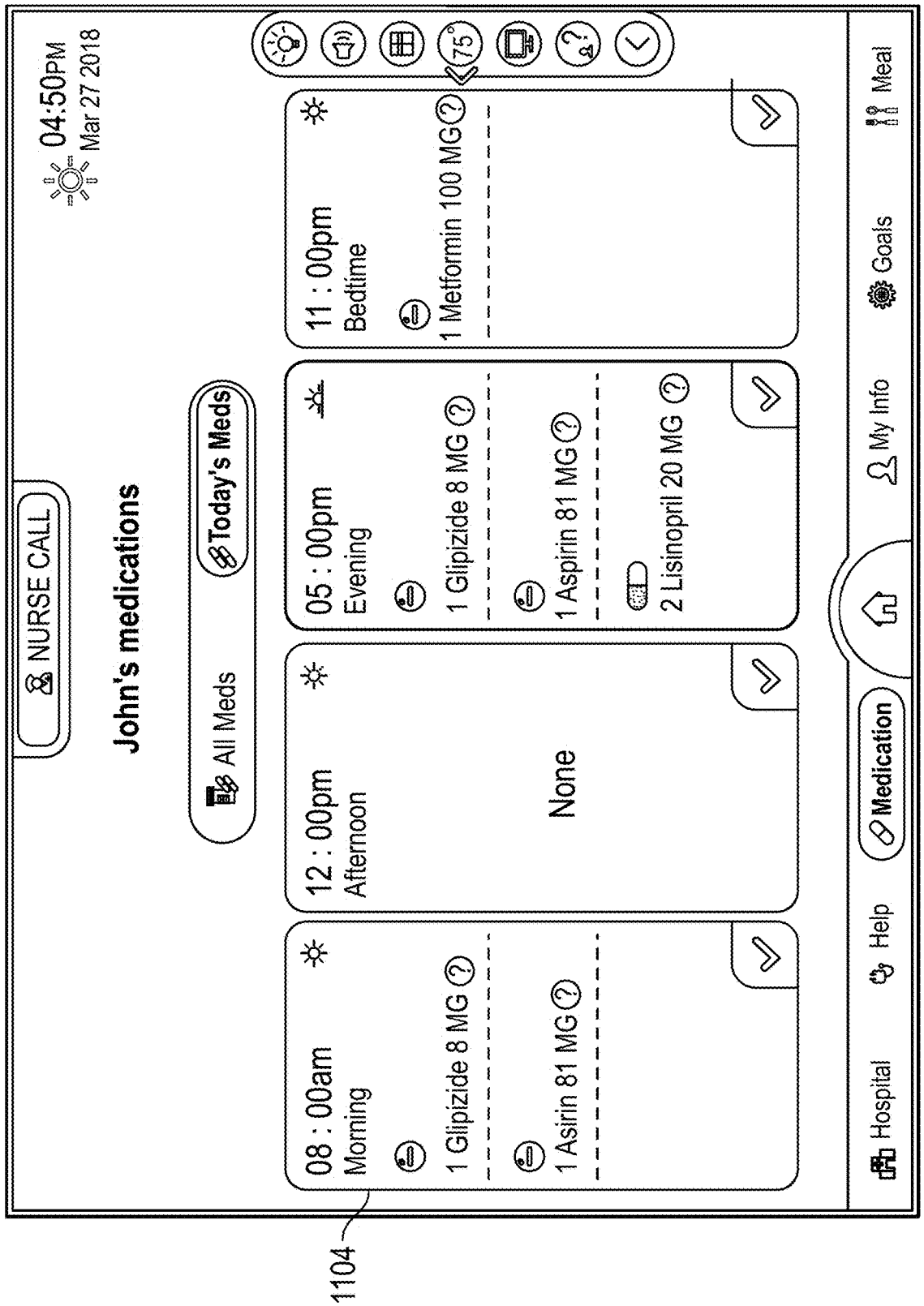

FIGS. 11A-11B show illustrative Medication tab sub-screens. FIG. 11A illustrates an example Medication tab default screen 1100. The Medication tab default screen 1100 may be accessed via the application navigation panel 205. The default screen 1100 may list all the patient's medications and related details, such as drug name 1101, administration schedule 1102, and dosage instructions 1103. The patient may also tap on individual drugs on the drug name list to view extra drug information, such as what the drug may treat, side effects of the drugs, and other information typically included on drug labels. In some configurations, an icon may be included that accurately reflects the physical form or appearance of the drug. FIG. 11B may offer a detailed view 1104 of the medication administration schedule 1102 for a given day, broken down by time and dosage. In some configurations, the detailed view 1104 displays medication information for the current day. In other configurations, the detailed view may include a date selection feature where patients can view their medication details for other dates. The detailed view 1104 may also include icons that show the physical form of the drugs. The information presented in the Medication tab sub-screens can not only help patients better understand what medications they are taking but can also act as a simple method for healthcare providers to confirm they are administering the correct medications.

Figure 12A:
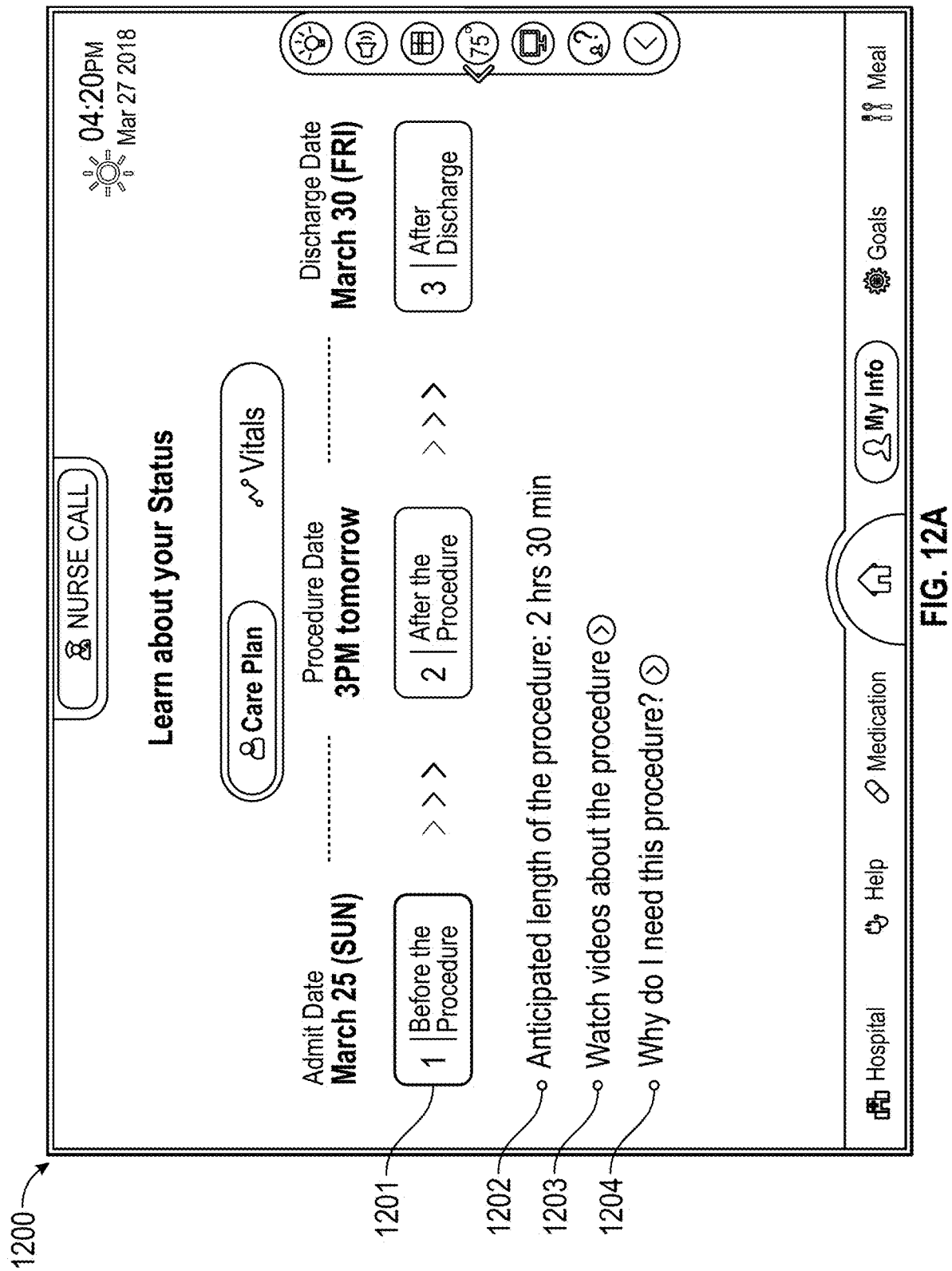
FIGS. 12A-12B are illustrative interfaces showing treatment details and patient vitals, according to some configurations.
Figure 12B:
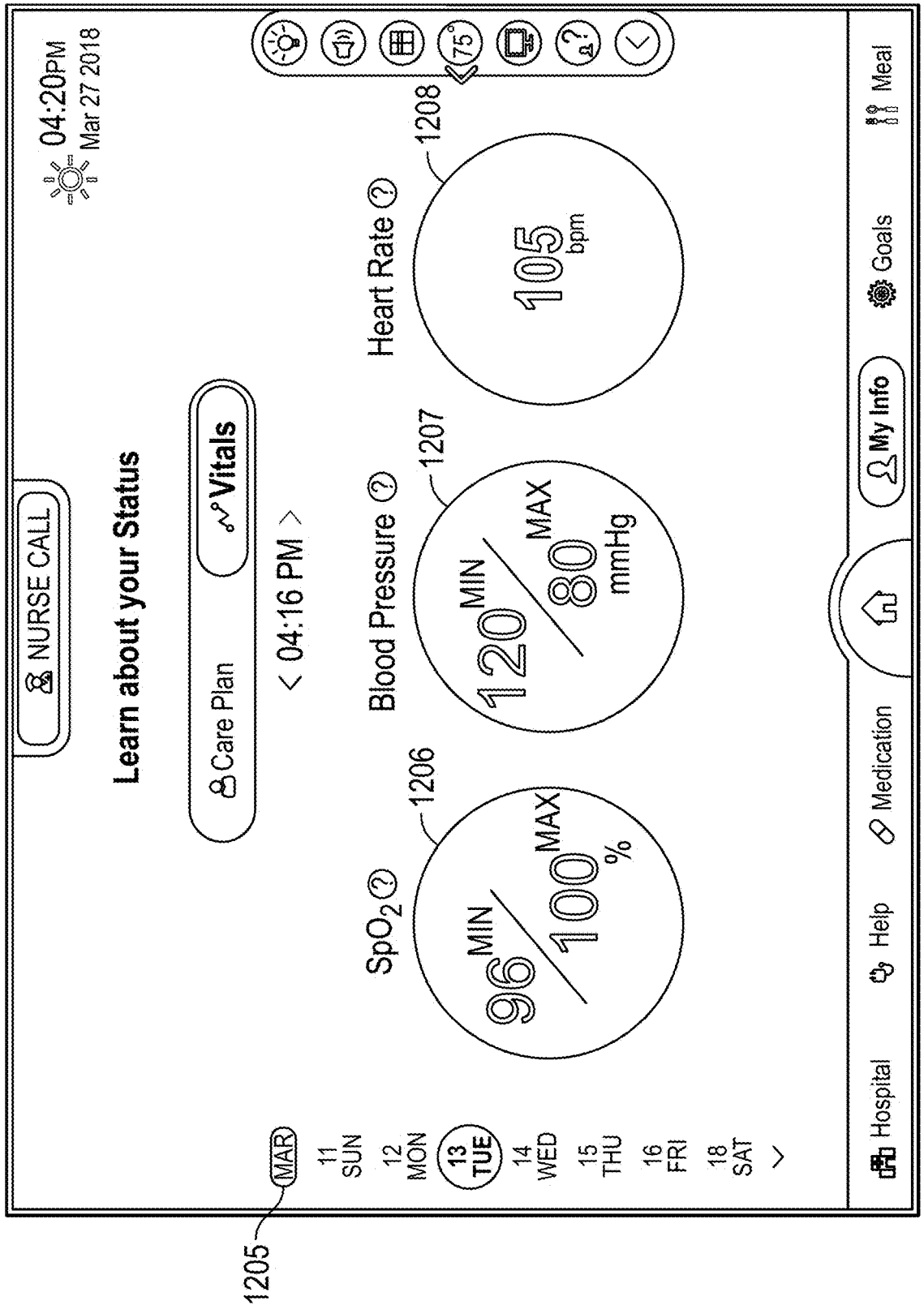

FIGS. 12A-12B show an illustrative My Info tab sub-screens. FIG. 12A illustrates an exemplary My Info tab default screen 1200, or Care Plan sub-screen, which may outline the patient's care plan. The My Info tab default screen 1200 may be accessed via the application navigation panel 205. The Care Plan sub-screen may show a procedure timeline 1201 and procedure details, including the length of the procedure 1202, videos about the procedure 1203, and why the procedure is necessary in the patient's case 1204. The procedure timeline 1201 may have buttons associated with each event on the timeline, and the patient may tap on each button to access an interactive sub-screen to learn more about each individual event. For example, a Before the Procedure sub-screen may allow the patient to access pre-approved informational videos by tapping on the button for videos about the procedure 1203. This provides approved information to patients, avoiding misinformation through a patient's own independent research, which can potentially carry the risk of finding the wrong procedure or being misinformed. Similar content may be incorporated in the other procedure timeline sub-screens. The content on the Care Plan sub-screen 1200 may also be customized for the patient. For example, a feature explaining why the procedure is necessary in the patient's case 1204 could be a short explanation personally drafted by the attending physician. Personalized explanations can help patients feels more at ease and more informed. FIG. 12B shows an example Vitals sub-screen, which may track the patient's oxygen levels 1206, blood pressure 1207, and heart rate 1208. The vitals may be recorded, so the patient can use the calendar panel 1205 to view trends.

Figure 13:
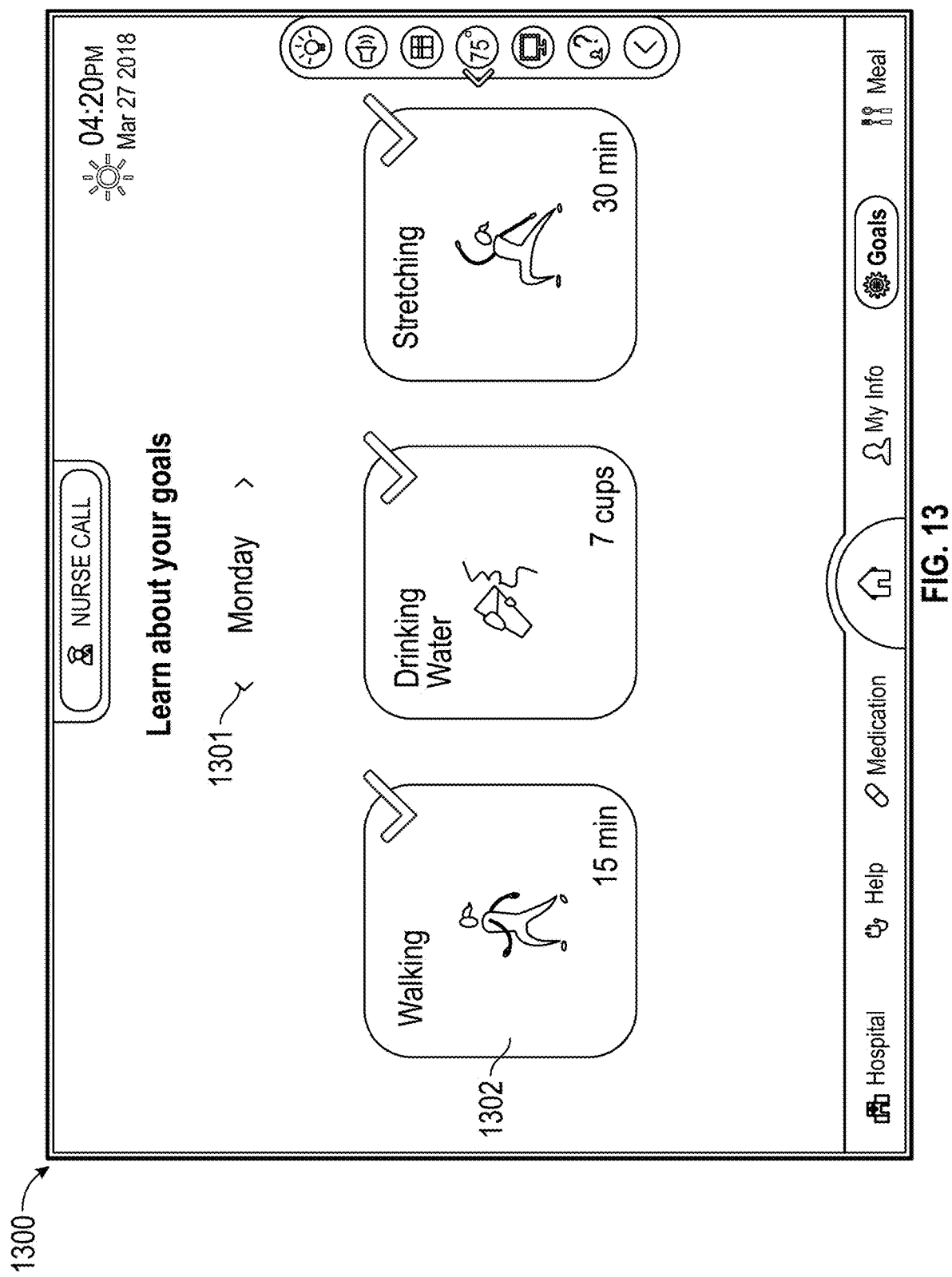
FIG. 13 is an illustrative interface showing a patient's daily goals, according to some configurations.

FIG. 13 illustrates an example default Goals tab screen 1300. Patients can check their daily tasks and completion statuses for those tasks. The Goals screen 1300 may be accessed via the application navigation panel 205. A date selector 1301 may allow patients to review old goals and see upcoming goals. The date selector 1301 may be a scroll-through list, a drop-down menu, a calendar graphic with selectable dates, or any other graphical representation that can allow the patient to view data from any date during the patient's hospital stay. The goals display 1302 may update to mark tasks as completed. Tasks may be marked completed by either patients or healthcare providers, or both.

Figure 14A:
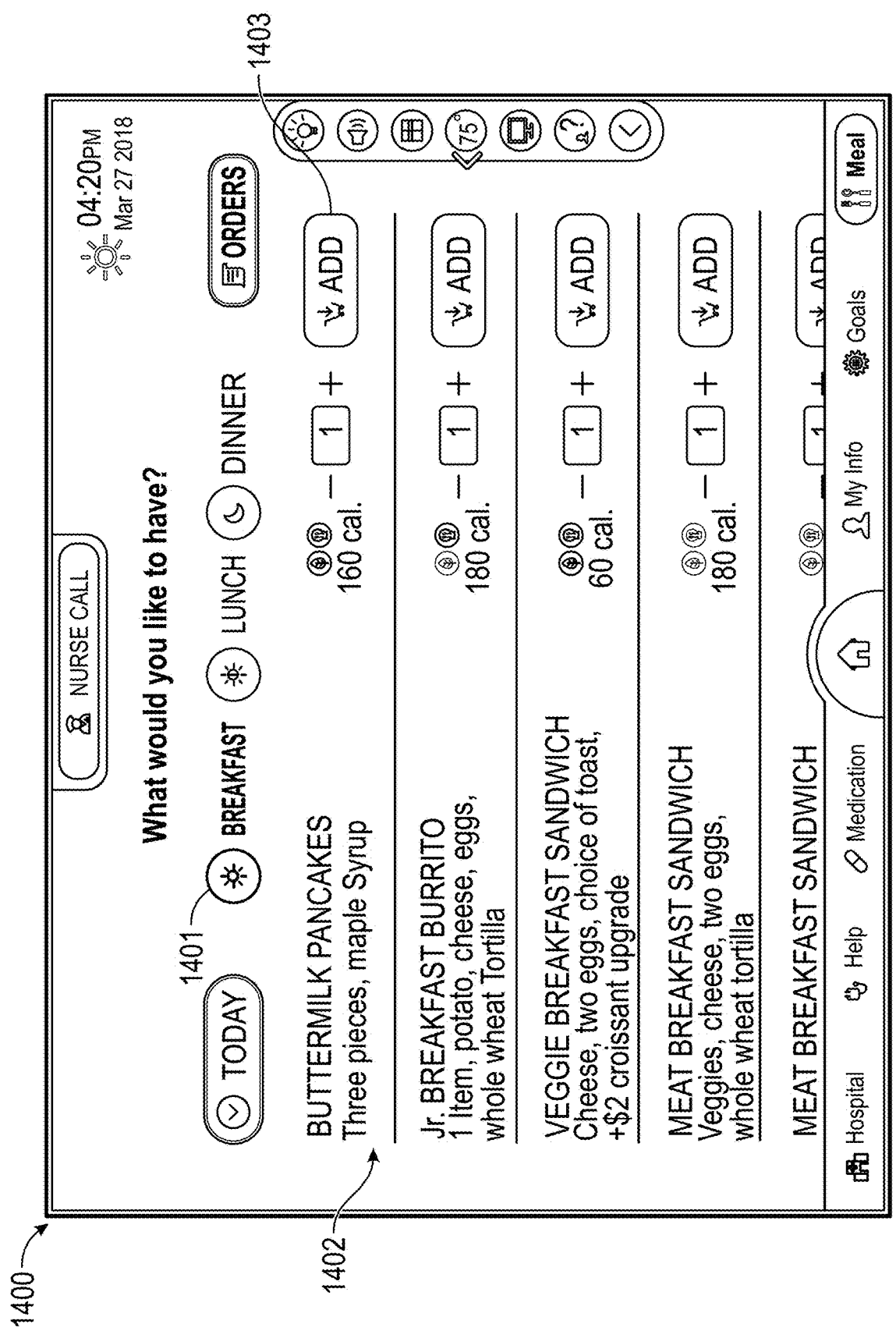
FIGS. 14A-14C are illustrative interfaces for a patient meal ordering feature, according to some configurations.
Figure 14B:
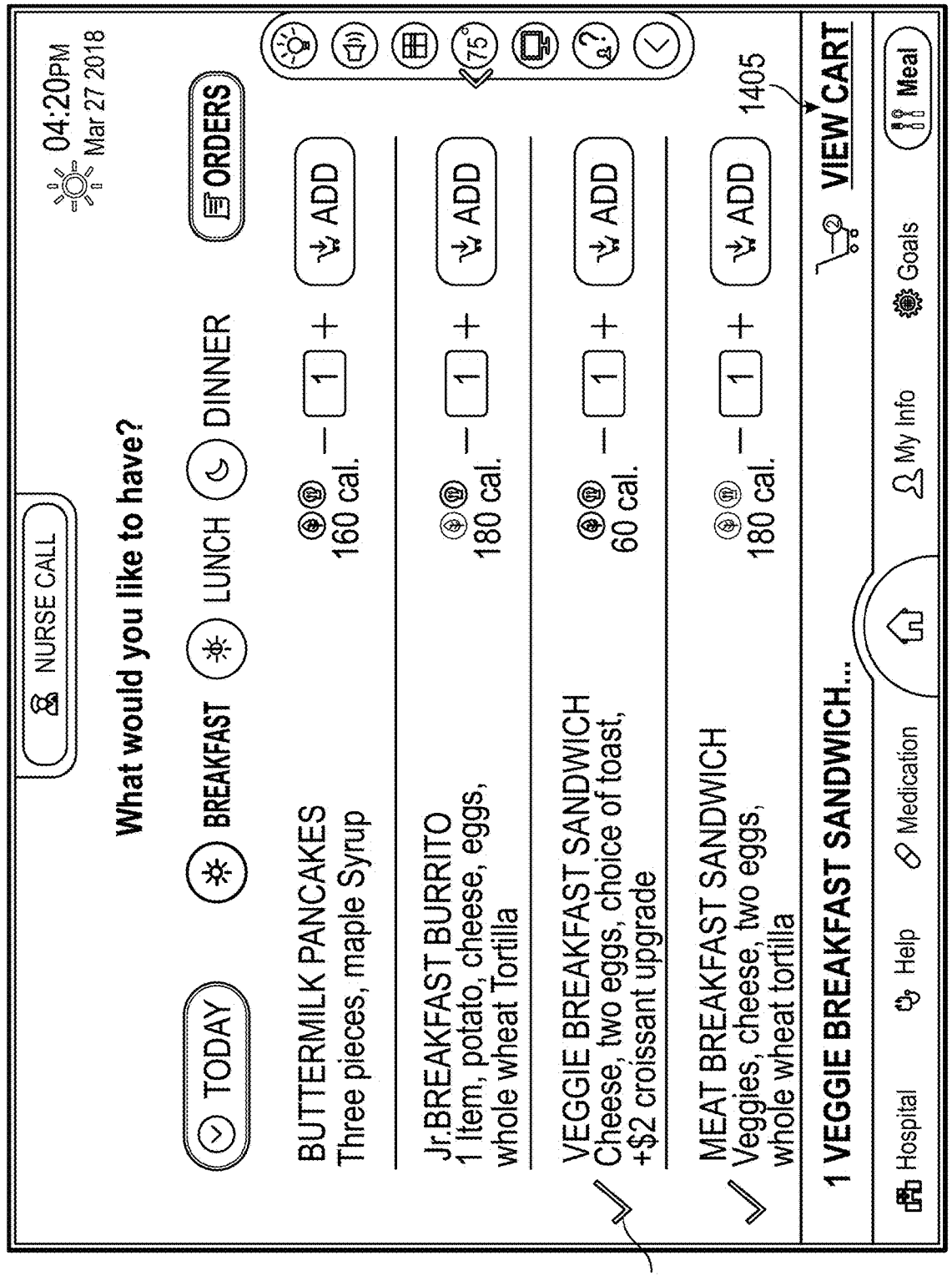
Figure 14C:
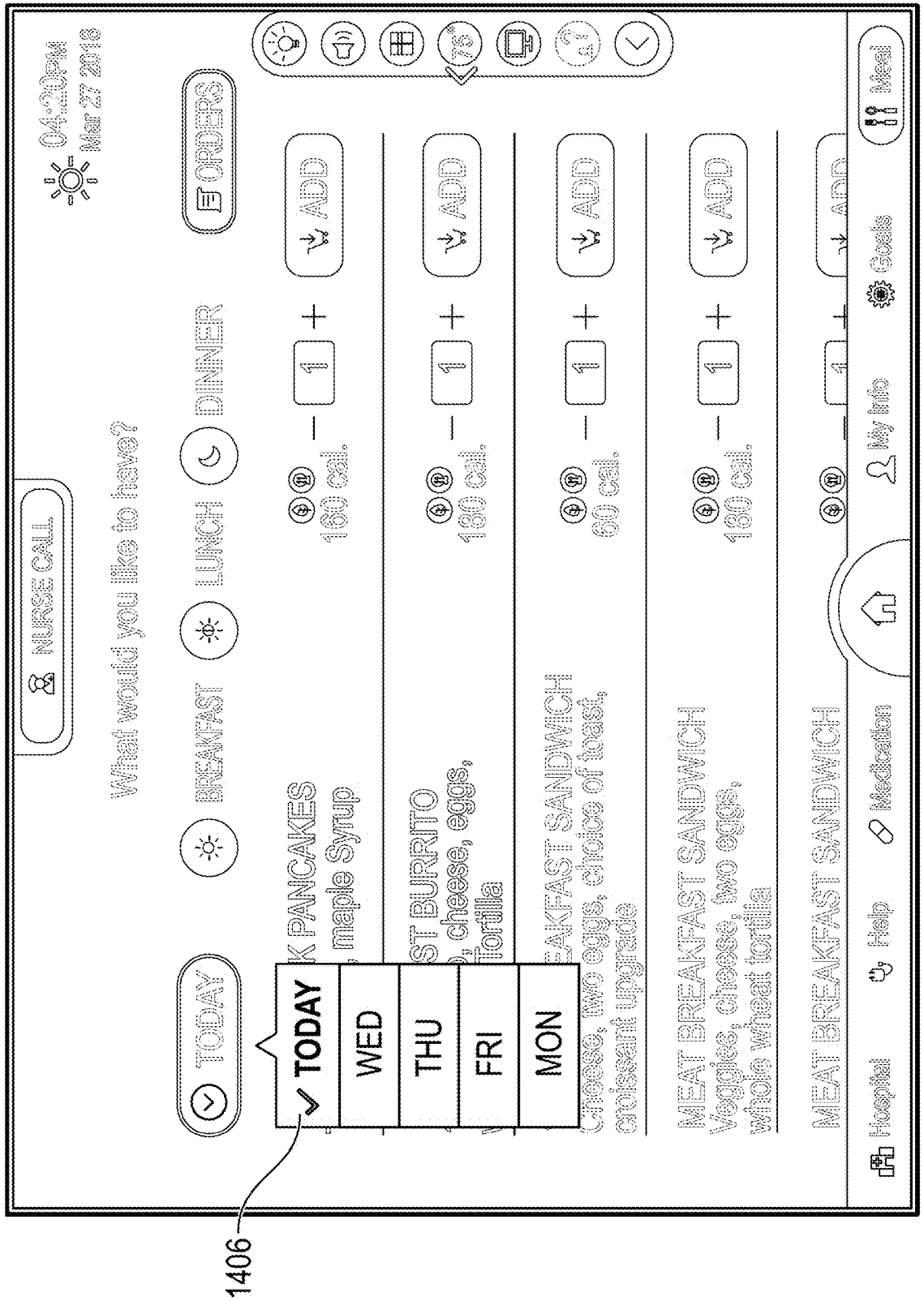

FIGS. 14A-14C show an exemplary Meal tab screen 1400 through which the patient can order food for any meal of the week. The Meal screen 1400 may be accessed via the application navigation panel 205. FIG. 14A shows an illustrative Meal tab screen 1400 before the patient places an order. The application may allow for meal selection 1401, so patients can order food for any meal of the day. The menu 1402 may list details about each dish, including, but not limited to, caloric and allergen information. When ready, the patient can tap the add button 1403 to add the dish to a virtual cart 1405. FIG. 14B shows an illustrative Meal tab screen 1400 after the patient has selected menu items. The selection graphic 1404 may update to show which dishes have been selected, and the patient can see the full list in a virtual cart 1405. FIG. 14C may show a date selection menu 1406 that the patient could use to order food for different days of the week. The date selection menu 1406 may be a scroll-through list, a drop-down menu, a calendar graphic with selectable dates, or any other graphical representation.

The various features and processes described above may be used independently of one another or may be combined in various ways. All possible combinations and sub-combinations are intended to fall within the scope of this disclosure. In addition, certain interfaces and features may be omitted in some implementations. The interfaces described herein are also not limited to any particular sequence and may be arranged in other sequences that are appropriate. Features may be added to or removed from the disclosed example configurations. The example systems and components described herein may be configured differently than described. For example, elements may be added to, removed from, or rearranged compared to the disclosed example configurations Conditional language, such as, among others, "can," "could," "might," or "may," unless specifically stated otherwise, or otherwise understood within the context as used, is generally intended to convey that certain configurations include, while other configurations do not include, certain features, elements and/or steps. Thus, such conditional language is not generally intended to imply that features, elements and/or steps are in any way required for one or more configurations or that one or more configurations necessarily include logic for deciding, with or without user input or prompting, whether these features, elements and/or steps are included or are to be performed in any particular configuration.

It should be emphasized that many variations and modifications may be made to the above-described configurations, the elements of which are to be understood as being among other acceptable examples. All such modifications and variations are intended to be included herein within the scope of this disclosure. The foregoing description details certain configurations of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A hospital patient assistance system comprising:
    a portable electronic device;
    said portable electronic device comprising a display and one or more hardware processors configured to:
        generate one or more graphical user interfaces for presentation on the display, said one or more graphical user interfaces configured to display a plurality of patient assistance options, wherein the patient assistance options includes an emergency nurse call feature and a non-emergency nurse call feature, wherein the emergency nurse call feature and the non-emergency nurse call feature are associated with different hospital departments such that selections of the emergency nurse call feature and the non-emergency nurse call feature are configured to transmit patient assistance requests to different devices associated with the different hospital departments.

2. The system of claim 1, wherein the one or more hardware processors are further configured to:
    receive, via the one or more graphical user interfaces, a user selection of one of the patient assistance options, each of the patient assistance options being based on a type of the emergency nurse call feature or the non-emergency nurse call feature requested by a patient;
    generate a patient assistance request, wherein the patient assistance request comprises the user selection;
    determine a recipient of the patient assistance request from a plurality of possible recipients based at least in part on the user selection; and
    wirelessly deliver the patient assistance request to a second electronic device, wherein the second electronic device is associated with the recipient.

3. The system of claim 1, wherein the one or more hardware processors are further configured to:
    receive data from a healthcare data network, wherein the data comprises healthcare and treatment regimen information;
    display the data from the healthcare data network in real time;
    track user progress throughout a treatment regimen; and
    update a representation of a living entity throughout the treatment regimen.

4. The system of claim 3, wherein the healthcare and treatment regimen information includes at least one of: treatment information personalized to the patient, or general educational materials.

5. The system of claim 1, wherein the one or more hardware processors are further configured to, in response to user input, interact with nearby electronically-controlled items.

6. The system of claim 3, wherein the living entity is a plant.

7. The system of claim 6, wherein the plant includes one or more leaves.

8. The system of claim 1, wherein the one or more user interfaces comprises icons selectable by the patient to indicating frequently used status indicators.

9. The system of claim 1, wherein a hospital room does not require physical switches for calling nurse.

10. The system of claim 1, wherein the patient assistance options further comprise a levels of pain feature allowing a user to indicate a level of pain which is communicated to a healthcare provider.

11. The system of claim 10, wherein the levels of pain feature communicates a level of pain to the healthcare provider when one or both of the emergency and non-emergency nurse call features are activated.

12. The system of claim 7, wherein updating the representation of the living entity comprises adding a leaf for each completed task.

13. The system of claim 7, wherein the plant further includes a flower, wherein updating the representation of the living entity further comprises displaying the flower blooming in response to all tasks being completed.

14. The system of claim 1, wherein, in response to receiving a user selection of a patient assistance option, the one or more hardware processors are further configured to activate a pop-up window or a sub-screen for a patient to enter details about the user selection.

15. The system of claim 14, wherein the pop-up window or the sub-screen includes preset options from which the patient may select to enter the details.

16. The system of claim 14, wherein the pop-up window or the sub-screen includes allows the patient to enter the details in free form.

17. The system of claim 1, wherein the emergency nurse call feature includes pain, nausea, device beeping, or any combinations thereof.

18. The system of claim 1, wherein the non-emergency nurse call feature includes toilet, water, cleaning, bedding, or any combinations thereof.

\* \* \* \* \*